United States Patent
Shirakura et al.

(10) Patent No.: US 9,545,445 B2
(45) Date of Patent: Jan. 17, 2017

(54) THERAPEUTIC DRUG FOR HYPERTENSION OR PREHYPERTENSION

(75) Inventors: Takashi Shirakura, Hino (JP); Mizuho Tamura, Hino (JP); Yoshimasa Takahashi, Hino (JP); Ippei Kuwahara, Sagamihara (JP)

(73) Assignee: Teijin Pharma Limited, Tokyo (JP)

( * ) Notice: Subject to any disclaimer, the term of this patent is extended or adjusted under 35 U.S.C. 154(b) by 0 days.

(21) Appl. No.: 12/823,715

(22) Filed: Jun. 25, 2010

(65) Prior Publication Data
US 2011/0046192 A1 Feb. 24, 2011

Related U.S. Application Data

(60) Provisional application No. 61/220,717, filed on Jun. 26, 2009.

(51) Int. Cl.
| | | |
|---|---|---|
| *A01N 43/78* | (2006.01) | |
| *A61K 31/425* | (2006.01) | |
| *A61K 45/06* | (2006.01) | |
| *A61K 31/426* | (2006.01) | |

(52) U.S. Cl.
CPC ............ *A61K 45/06* (2013.01); *A61K 31/426* (2013.01)

(58) Field of Classification Search
CPC ... A61K 31/426; A61K 45/06; A61K 2300/00
USPC .................................................. 514/370, 365
See application file for complete search history.

(56) References Cited

U.S. PATENT DOCUMENTS

| 2002/0019360 A1 | 2/2002 | Kivlighn et al. |
| 2007/0167454 A1* | 7/2007 | Lademacher et al. ........ 514/246 |
| 2010/0137281 A1 | 6/2010 | Kuroita et al. |

FOREIGN PATENT DOCUMENTS

| EP | 0 513 379 A1 | 11/1992 |
| JP | 2009-503034 A | 1/2009 |
| JP | 2009-503094 A | 1/2009 |
| WO | 92/09279 A1 | 6/1992 |
| WO | 2007/019153 A2 | 2/2007 |
| WO | 2008/143262 A1 | 11/2008 |

OTHER PUBLICATIONS

Takahashi et al. (Ann Rheum Dis 2003, 62, 572-575).*
Meredith ( BJC, May/Jun. 2010, 17, 2).*
Manuel T. Velasquez., "Angiotensin II receptor blockers. A new class of Antihypertensive Drugs," Arch Fam Med., Jun. 1996, pp. 351-356, vol. 5, No. 6.
Frans H.H. Leenen, et al., "Comparison of the Effects of Amlodipine and Diltiazem on 24-Hour Blood Pressure, Plasma Catecholamines, and Left Ventricular Mass," Am J. Cardiol, Jul. 1996, pp. 203-207, vol. 78, No. 2.
John S. Bomalaski, MD, et al., "Serum Uric Acid-Lowering Therapies: Where are we heading in Management of Hyperuricemia and the Potential Role of Uricase," Curr. Rheumatol Rep., 2004, pp. 240-247, vol. 6, No. 3.
Jing Fang, et al., "Hypertension Control at Physicians' Offices in the United States," American Journal of Hypertension, Feb. 2008, pp. 136-142, vol. 21, No. 2.
Luca De Nicola, et al., "Management of Hypertension in Chronic Kidney Disease: The Italian Multicentric Study," J. Nephrol, Jun. 2005, pp. 397-404, vol. 18, No. 4.
James H. Jackson, Pharmad, MPH, et al., "Blood Pressure Control and Pharmacotherapy Patterns in the United States Before and After the Release of the Joint National Committee on the Prevention, Detection, Evaluation, and Treatment of High Blood Pressure (JNC 7) Guidelines," JABFM, Nov.-Dec. 2008, pp. 512-521, vol. 21, No. 6.
Shawna D. Nesbitt, MD, MS, "Antihypertensive Combination Therapy: Optimizing Blood Pressure Control and Cardiovascular Risk Reduction," The Journal of Clinical Hypertension, Nov. 2007, pp. 26-32, Supp. 4, vol. 9, No. 11.
Kenneth Jamerson, M.D., et al., "Benazepril Plus Amlodipine or Hydrochlorothiazide for Hypertension in High-Risk Patients," The New England Journal of Medicine, Dec. 4, 2008, pp. 2417-2428, vol. 359, No. 23.
John Chalmers, "The Importance of Drug Combination for Effective Control of Hypertension," Clin. And Exper. Hypertension, 1999, pp. 875-884, vol. 21, No. 5 & 6.
Yeouda Edoute, et al., "Cardiovascular Adverse Drug Reaction Associated with Combined β-Adrenergic and Calcium Entry-Blocking Agents," Journal of Cardiovascular Pharmacology, 2000, pp. 556-559, vol. 35, No. 4.

(Continued)

*Primary Examiner* — Uma Ramachandran
(74) *Attorney, Agent, or Firm* — Sughrue Mion, PLLC

(57) ABSTRACT

The present invention relates to a therapeutic drug or a preventive drug for hypertension or high-normal blood pressure, comprising (a) and (b) as active ingredients:
(a) a 2-phenylthiazole compound represented by formula (I) or a pharmaceutically acceptable salt thereof;

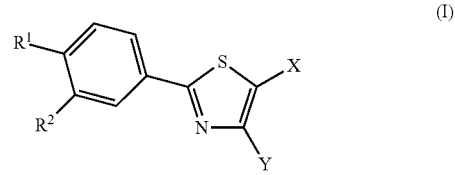

(b) at least one compound or a pharmaceutically acceptable salt thereof selected from the group consisting of calcium antagonists, renin-angiotensin system inhibitors, diuretics, sympatholytic agents, vasodilators, and medicinally acceptable salts of these.

The present invention also relates to a therapeutic method or a preventive method for hypertension or high-normal blood pressure, comprising administering the above (a) and (b) in amounts effective for treating or preventing hypertension or high-normal blood pressure.

4 Claims, No Drawings

(56) References Cited

OTHER PUBLICATIONS

James M. Mason, et al., "The Diabetogenic Potential of Thiazide-Type Diuretic and Beta-Blocker Combinations in Patients with Hypertension," Journal of Hypertension, 2005, pp. 1777-1781, vol. 23, No. 10.

International Search Report of PCT/JP2010/061301 dated Aug. 24, 2010.

Mexican Office Action issued on Mar. 4, 2013 in a corresponding Mexican Patent Application No. MX/a/2011/013541.

Chobanian et al., "The Seventh Report of the Joint National Committee on Prevention, Detection, Evaluation, and Treatment of High Blood Pressure: The JNC 7 Report," JAMA (the Journal of the American Medical Association), American Medical Association, May 14, 2003, pp. 2560-2572.

Chobanian et al., "The Seventh Report of the Joint National Committee on Prevention, Detection, Evaluation, and Treatment of High Blood Pressure: The JNC 7 Report," JAMA (the Journal of the American Medical Association), American Medical Association, May 14, 2003, pp. 3560-3572.

Extended European Search Report issued on Nov. 20, 2012 from the European Patent Office in corresponding European Application No. 10 792 238.7.

Office Action dated Apr. 25, 2014 from the Taiwanese Patent Office in Taiwanese Application No. 099120829.

Official Action dated Apr. 10, 2014, issued by the Russian Patent Office in Russian Application No. 2012102518.

I. B. Mikhailov, *Reference Book for a Doctor: Clinical Pharmacology*, S—Pb, Foliant, 2001, p. 355, Chapter 11.5.

Reference Book VIDAL, Russian Medications 2008, Astrapharmservice, pp. B-591-B-592, Irumed Article.

Australian Office Action issued on Mar. 4, 2014 from the Australian Patent Office in Australian Application No. 2010263549.

New Pharmacology (4th version), 2002, pp. 393-402.

Sànchez-Lozada et al., "Effects of febuxostat on metabolic and renal alterations in rats with fructose-induced metabolic syndrome", Am J Physiol Renal Physiol., Apr. 2008, vol. 294, pp. F710-F718 (9 pages total).

\* cited by examiner

THERAPEUTIC DRUG FOR HYPERTENSION OR PREHYPERTENSION

CROSS-REFERENCE TO RELATED APPLICATION

This application relates to and claims the benefit of priority from U.S. Provisional Application No. 61/220,717 filed on Jun. 26, 2009 the entire disclosure of which is incorporated herein by reference.

TECHNICAL FIELD

The present invention relates to a therapeutic drug or a preventive drug for hypertension or high-normal blood pressure, or to a therapeutic method or a preventive method for the same.

BACKGROUND ART

As drugs for treating hypertension, many drugs are being used, such as calcium antagonists, renin-angiotensin system inhibitors (angiotensin-converting-enzyme (ACE) inhibitors and angiotensin receptor antagonists), diuretics, sympatholytic agents (α-blockers, β-blockers, and αβ-blockers), vasodilators, and the like.

Despite the presence of these many hypotensive drugs, in the actual clinical practice the proportion of patients who have attained the target level of blood pressure is as low as about 40% (NPL 1). Above all, with high-risk patients having backgrounds such as advanced age, diabetes, renal disorder, long period of suffering from hypertension, and the like, the proportion of patients who attain the target blood pressure level is still lower (NPL 2). Therefore, in the recent guidelines for hypertension, a concomitant treatment with two or more kinds of drugs is recommended and actually the number of cases of concomitant treatment is increasing (NPL 3). There are more than a few cases where three or more kinds of drugs are used concomitantly in order to attain the target blood pressure level (NPL 4). However, in the concomitant use of existing hypotensive drugs, it is known that no additive hypotensive effect is obtained in combined use of, for example, an ACE inhibitor and β-blocker, and in a concomitant use of an ACE inhibitor and angiotensin receptor antagonist (NPL5 and 6). In addition, there is a possibility that adverse drug reactions of each drug become pronounced by the concomitant use, such as bradycardia observed in the combined use of diltiazem, a calcium antagonist and a β-blocker, and metabolic disorders including elevated uric acid level, high blood sugar level, lipid abnormality, and the like seen in the concomitant use of a diuretic and β-blocker (NPL 7 and 8). Therefore, in order to open up treatment options, a drug is desired, which has less adverse drug reactions and has a mechanism different from that of the existing hypotensive drugs.

It has become clear that 2-(3-cyano-4-isobutyloxyphenyl)-4-methyl-5-thiazolecarboxylic acid or its medicinally acceptable salt, which has a uric acid lowering effect, shows a hypotensive effect by a mechanism different from the existing hypotensive drugs (PTL 1).

CITATION LIST

Patent Literature

PTL 1: Japanese National Phase PCT Laid-Open Publication No. 2009-503094

Non Patent Literature

NPL 1: American Journal of Hypertension. 2008; 21: 136-142
NPL 2: Journal of Nephrology. 2005; 18: 397-404
NPL 3: The Journal of the American Board of Family Medicine. 2008; 21: 512-521
NPL 4: Journal of Clinical Hypertension. 2007; 9: 26-32
NPL 5: New England Journal of Medicine. 2008; 359: 2417-2428
NPL 6: Clinical and Experimental Hypertension. 1999; 21: 875-884
NPL 7: Journal of Cardiovascular Pharmacology. 2000; 35: 556-559
NPL 8: Journal of Hypertension. 2005; 23: 1777-1781

SUMMARY OF INVENTION

Technical Problem

An object of the present invention is to provide a therapeutic drug or a preventive drug for hypertension or high-normal blood pressure, wherein the drug shows, through a mechanism different from the existing drugs, a stronger hypotensive effect or less adverse drug reactions by concomitant use with other hypotensive drugs. Furthermore, another object of the present invention is to provide a therapeutic method or a preventive method for hypertension or high-normal blood pressure, wherein the drug shows, through a mechanism different from the existing drugs, a stronger hypotensive effect or less adverse drug reactions by concomitant use with other hypotensive drugs.

Solution to Problem

The present inventors have made diligent studies to solve the above problem and have found that specific agents, which can each be used alone, provide much higher drug efficacy when used in combination than when used either alone.

That is, the present invention relates to a therapeutic drug or a preventive drug for hypertension or high-normal blood pressure, comprising the following (a) and (b) as active ingredients:

(a) a 2-phenylthiazole compound represented by formula (I):

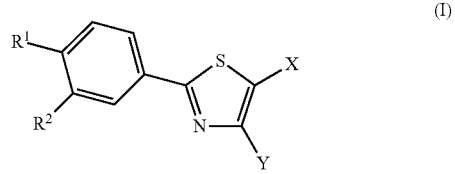

wherein
$R^1$ represents a $C_{1-8}$ alkoxy group, a morpholino group, a 4-methylpiperazin-1-yl group, or a piperidino group;
$R^2$ represents a nitro group or a cyano group;
X represents a carboxyl group or a $C_{2-7}$ alkoxycarbonyl group; and
Y represents a hydrogen atom or a $C_{1-6}$ alkyl group;
or a pharmaceutically acceptable salt thereof; and
(b) at least one compound selected from the group consisting of calcium antagonists, renin-angiotensin system inhibitors, diuretics, sympatholytic agents, vasodilators, and pharmaceutically acceptable salts thereof.

The present invention also relates to a therapeutic drug or a preventive drug for hypertension or high-normal blood pressure, comprising the above (a) and (b) as active ingredients, which constitute a combination drug or are each independent single drugs.

The present invention further relates to a therapeutic drug or a preventive drug for hypertension or high-normal blood pressure, comprising the above (a) and (b) as active ingredients, which constitute a kit.

The present invention also relates to a therapeutic method or a preventive method for hypertension or high-normal blood pressure, comprising administering the above (a) and (b) in amounts effective for treating or preventing hypertension or high-normal blood pressure.

Advantageous Effects of Invention

According to the present invention, much more potent therapeutic or preventive effects can be obtained by administering both active ingredients (a) and (b) in combination than by using either alone.

DESCRIPTION OF EMBODIMENTS

The active ingredient (a) used in the present invention is a 2-phenylthiazole compound represented by formula (I):

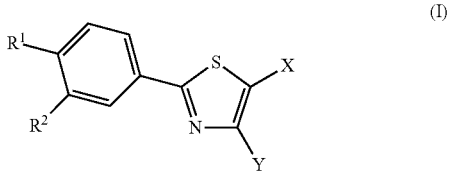

wherein
R$^1$ represents a C$_{1-8}$ alkoxy group, a morpholino group, a 4-methylpiperazin-1-yl group or a piperidino group;
R$^2$ represents a nitro group or a cyano group;
X represents a carboxyl group or a C$_{2-7}$ alkoxycarbonyl group; and
Y represents a hydrogen atom or a C$_{1-6}$ alkyl group;
or a pharmaceutically acceptable salt thereof.

The active ingredient (a) is, for example, 2-(3-cyano-4-isobutyloxyphenyl)-4-methyl-5-thiazolecarboxylic acid (generic name: febuxostat), a compound which can be produced by a known method such as the method described in WO 92/09279.

The active ingredient (b) used in the present invention is at least one compound selected from the group consisting of calcium antagonists, renin-angiotensin system inhibitors, diuretics, sympatholytic agents, vasodilators, or a pharmaceutically acceptable salt thereof.

Calcium antagonists are agents which lower blood pressure by preventing the entry of calcium into smooth muscle cells that make up peripheral blood vessels, and thereby dilating blood vessels. Calcium antagonists include, for example, amlodipine, nifedipine, nisoldipine, nitrendipine, nicardipine, nilvadipine, azelnidipine, manidipine, efonidipine, cilnidipine, aranidipine, benidipine, felodipine, barnidipine, diltiazem, isradipine and verapamil, among which amlodipine, nifedipine, diltiazem, felodipine, cilnidipine and azelnidipine are preferred, and amlodipine, nifedipine and diltiazem are more preferred.

Renin-angiotensin system inhibitors include angiotensin receptor blockers (ARBs), which specifically bind to the angiotensin II receptor and thereby suppress vasoconstriction, fluid retention and sympathetic excitation caused by the action of the angiotensin II; angiotensin-converting enzyme (ACE) inhibitors, which prevent blood pressure from rising by suppressing the production of angiotensin II that raises blood pressure; and renin inhibitors, which prevent blood pressure from rising by suppressing the conversion of angiotensinogen to angiotensin I. ARBs include, for example, losartan, candesartan, valsartan, telmisartan, olmesartan, irbesartan, pratosartan and eprosartan, among which valsartan, losartan, candesartan, irbesartan, telmisartan and olmesartan are preferred, and losartan and candesartan are more preferred. ACE inhibitors include, for example, captopril, enalapril, perindopril, lisinopril, alacepril, delapril, benazepril, cilazapril, imidapril, temocapril, quinapril, trandolapril, ramipril, fosinopril and moexipril, among which ramipril, enalapril, quinapril, lisinopril, perindopril and imidapril are preferred, and ramipril and enalapril are more preferred. Renin inhibitors include, for example, aliskiren.

Diuretics are agents which lower blood pressure by acting on kidneys to increase sodium and water excretion and thereby reduce the body fluid and the circulating blood volumes. Diuretics include, for example, trichlormethiazide, hydrochlorothiazide, benzylhydrochlorothiazide, indapamide, mefruside, chlorthalidone, tripamide, meticrane, triamteren, furosemide, eplerenone, spironolactone, chlorothiazide, metolazone, hydroflumethiazide, methyclothiazide, polythiazide, bumetanide, ethacrynic acid, torsemide and amiloride, among which hydrochlorothiazide, chlorthalidone, trichlormethiazide, furosemide, eplerenone and spironolactone are preferred.

Sympatholytic agents include α-blockers, β-blockers, αβ-blockers, and centrally acting sympatholytic agents. α-Blockers are agents which lower blood pressure by suppressing the constriction of peripheral blood vessels and thereby dilating blood vessels. β-Blockers are agents which lower blood pressure by lowering heart rate and cardiac output. α-Blockers include, for example, doxazosin, bunazosin, terazosin, prazosin, urapidil, alfuzosin, phenoxybenzamine and phentolamine, among which alfuzosin and urapidil are preferred. β-Blockers include, for example, atenolol, bisoprolol, betaxolol, metoprolol, acebutolol, celiprolol, propranolol, nipradilol, tilisolol, nadolol, carteolol, pindolol, penbutolol, bopindolol, timolol and esmolol, among which metoprolol, bisoprolol, atenolol and propranolol are preferred. αβ-Blockers include, for example, carbedilol, amosulalol, arotinolol, labetalol and bevantolol, among which carbedilol is preferred. Centrally acting sympatholytic agents are agents which lower blood pressure by stimulating α2-receptors in the vasomotor center and thereby suppressing sympathetic nerve activity. Centrally acting sympatholytic agents include, for example, clonidine, guanabenz, guanfacine, and methyldopa.

Vasodilators are agents which lower blood pressure by acting directly on vascular smooth muscle to dilate blood vessels. Vasodilators include, for example, hydralazine, todralazine, budralazine, cadralazine, and minoxidil.

If desired, the active ingredients (a) and (b) can be converted to their pharmaceutically acceptable salts. Such salts include, for example, salts with inorganic acids such as hydrochloric acid, hydrobromic acid, hydriodic acid, sulfuric acid, nitric acid, phosphoric acid, and carbonic acid; salts with organic acids such as formic acid, acetic acid, propionic acid, trifluoroacetic acid, phthalic acid, oxalic acid, malonic acid, succinic acid, fumaric acid, maleic acid, lactic acid, malic acid, tartaric acid, citric acid, benzoic acid, methanesulfonic acid, ethanesulfonic acid, benzenesulfonic acid, and p-toluenesulfonic acid; salts with amino acids such as lysine, arginine, ornithine, glutamic acid, and aspartic acid; salts with alkali metals such as sodium, potassium, and lithium; salts with alkaline-earth metals such as calcium and magnesium; salts with metals such as aluminum, zinc, and iron; salts with organic bases such as methylamine, ethylamine, t-octylamine, diethylamine, trimethylamine, triethylamine, ethylenediamine, piperidine, piperazine, pyridine, picoline, ethanolamine, diethanolamine, triethanolamine, cyclo hexylamine, dicyclohexylamine, N-methyl glucamine, tris(hydroxymethyl)aminomethane, and N,N'-dibenzylethylenediamine; ammonium salts; and the like.

The doses of the active ingredients of the present invention are effective doses for the treatment or prevention of hypertension, and may depend on the age and weight of a patient, the type of combination therapy, the frequency of treatment, the type of desired effect, the method of administration, or the like.

The therapeutic or preventive drug of the present invention has only to comprise an active ingredient (a) or its pharmaceutically acceptable salt, and an active ingredient (b) or its pharmaceutically acceptable salt. These active ingredients may be mixed together and administered simultaneously, or may be administered separately at the same time or in succession, or separately at a certain interval. When not administered simultaneously, the active ingredients may be administered alternately with each other, or one of the active ingredients may be administered continuously before the other is administered, for example.

The therapeutic or preventive drug of the present invention may take any form, as long as it comprises an active ingredient (a) or its pharmaceutically acceptable salt, and an active ingredient (b) or its pharmaceutically acceptable salt. For example, the active ingredients may both constitute a combination drug, or may each constitute an independent single drug. As used herein, "combination drug" refers to a pharmaceutical preparation containing two or more active ingredients, while "single drug" refers to a pharmaceutical preparation containing one active ingredient.

The therapeutic or preventive drug or the therapeutic or preventive method of the present invention in which both active ingredients are single drugs means a drug or a method in which single drugs that can each be utilized alone are utilized in combination. Thus, the drugs containing the active ingredients, respectively, may take different dosage forms. For example, the forms of these drugs may be solid or liquid, or may be solid and liquid; the dosage forms are not particularly limited. In addition, the routes of administration of these drugs may be the same or different. When both active ingredients are single drugs, the drugs may be provided in a kit form containing a set of them. Representative kit forms include a blister package in which both drugs in quantities required for a specific period (for example, a period of a week or more) in accordance with a dosing schedule are packaged together in one sheet, and the like. Further, these drugs may be packaged in the same package such as PTP at the final stage in the manufacture of the drugs, or may be put into the same bag at the time of prescription in a hospital, a pharmacy, and the like; the kit forms are not particularly limited.

As a combination drug, for example, the active ingredients in amounts suitable for them to exert their respective effects may be combined together to manufacture a dosage form such as tablet, capsule, and liquid preparation. The time of combining the active ingredients together to form a combination drug may be at the stage of manufacture of a dosage form for a combination drug, or may be immediately before administration. When combined at the manufacturing stage, for example, the active ingredients may be mixed together in suitable amounts, then shaped and packaged. The method of shaping is not particularly limited; the agents may be mixed together or may be laminated in layers, for example. When a combination drug is prepared immediately before administration, a possible method is, for example, to store the active ingredients independently from each other until just before administration and, at the time of administration, mix together the agents in liquid form, or dissolve one of the agents in solid form such as tablet, pill, granule, powder or capsule in the other in liquid form, or mix together the agents in solid form such as granule or powder. The method of mixing the active ingredients immediately before administration may be to mix them by hand, or to use a package that allows mixing them together simply by cutting, pulling, splitting or the like. The forms of the combination drug include dosage forms such as tablet, pill, granule, powder, liquid preparation, suspension, syrup, or capsule.

The therapeutic or preventive drug of the present invention may be administered daily or intermittently, and the daily dosage can be administered once daily or divided into two or three doses. When both active ingredients are single drugs, the numbers of their doses may be the same or different. Further, when both agents are single drugs, the numbers of their doses may be a combination of the numbers of times each of them is usually administered. Even in the case where different numbers of doses are selected for each drug as just mentioned above, an improvement in convenience can be expected if they are provided in a kit form such as blister package.

The therapeutic or preventive drug of the present invention can be prepared by a known method from their active ingredients only, or together with suitable additives as described below. Specific examples of such dosage forms include oral preparations such as soft capsule, hard capsule, tablet and syrup, injections, or external preparations.

A pharmaceutical preparation containing the active ingredients of the present invention may be prepared using additives normally used in formulating pharmaceutical preparations. Those additives include, in the case of a solid pharmaceutical preparation, an excipient such as lactose, sucrose, glucose, cornstarch, potato starch, crystalline cellulose, light anhydrous silicic acid, synthetic aluminum silicate, magnesium aluminometasilicate, and calcium hydrogen phosphate; a binder such as crystalline cellulose, carboxymethyl cellulose, hydroxypropylcellulose, sodium carboxymethylcellulose, and polyvinylpyrrolidone; a disintegrant such as starch, sodium carboxymethylcellulose, calcium carboxymethylcellulose, croscarmellose sodium, and sodium carboxymethyl starch; a lubricant such as talc and stearates; a coating agent such as hydroxymethylpropylcellulose, hydroxypropylmethylcellulose phthalate, and ethylcellulose; a coloring agent; in the case of a semisolid pharmaceutical preparation, a base such as white petrolatum; in the case of a liquid pharmaceutical preparation, a solvent such as ethanol; a solubilizing agent such as ethanol; a preservative such as p-hydroxybenzoate esters; an isotonization agent such as glucose; a buffering agent such as citrates; an antioxidant such as L-ascorbic acid; a chelating agent such as EDTA; a suspending agent/an emulsifier such as polysorbate 80; and the like.

The hypertension in the present invention is defined as a systolic blood pressure of 140 mmHg or above and/or a diastolic blood pressure of 90 mmHg or above. The high-normal blood pressure in the present invention is defined as a systolic blood pressure of 130 mmHg or above but less than 140 mmHg and/or a diastolic blood pressure of 85 mmHg or above but less than 90 mmHg.

EXAMPLES

Example 1

The effect of the combination of febuxostat and antihypertensive agent (b) on spontaneously hypertensive models was confirmed. In this case, losartan (an angiotensin-receptor antagonist), enalapril (an angiotensin-converting enzyme inhibitor), amlodipine (a calcium channel blocker), and diltiazem (a calcium channel blocker) were used as representative examples of the antihypertensive agent (b). Twelve-week-old male SHRs (Spontaneously Hypertensive Rats) were used for experiment after subjecting them to quarantine for 1 week or more. At 15 or 16 weeks old, the SHRs were trained for blood pressure measurement with a Tail-Cuff method sphygmomanometer (BP-2000, Visitech systems, Napa Place, N.C., USA) for 1 to 2 weeks. After completing the training, they underwent blood pressure measurement at 17 to 18 weeks old. The animals were divided into 4 groups (10 for each) by taking care not to cause a bias in the systolic blood pressure, and the drug administration was started. Tap water was administered to a first group as a control group. A solution of each test material dissolved in tap water was administered to second to fourth groups. That is, febuxostat was administered to the second group, each antihypertensive agent of losartan, enalapril, amlodipine or diltiazem to the third group, and the mixture of febuxostat and the antihypertensive agents administered to the third group as combined administration to the fourth group. The dose of each agent was calculated from the concentration in the solution, the amount of drinking water, and the weight of the rats. After administration was carried out for 2 to 6 weeks, the value of their systolic blood pressure were measured by Tail-Cuff method. Tables 1 to 4 show the group formation, the test materials and the dose thereof per day, the measured values of systolic blood pressure (mean value±standard error: mmHg). This evaluation confirmed the antihypertensive action of administration of febuxostat or the antihypertensive agent (b) alone and the synergistic antihypertensive action of the combined administration of febuxostat and the antihypertensive agent (b).

TABLE 1

Effect of Febuxostat, Losartan and Combination Thereof on Blood Pressure

| Group | Test material and dose | | | |
|---|---|---|---|---|
| Group 1 | tap water | | | |
| Group 2 | febuxostat 3 mg/kg/day | | | |
| Group 3 | losartan 3 mg/kg/day | | | |
| Group 4 | febuxostat 3 mg/kg/day + losartan 3 mg/kg/day | | | |
| | Group 1 | Group 2 | Group 3 | Group 4 |
| Before administration | 230 ± 4 | 230 ± 4 | 232 ± 4 | 230 ± 2 |
| 14th day after administration | 233 ± 4 | 219 ± 4 | 215 ± 2 | 198 ± 3 |

TABLE 2

Effect of Febuxostat, Enalapril and Combination Thereof on Blood Pressure

| Group | Test material and dose | | | |
|---|---|---|---|---|
| Group 1 | tap water | | | |
| Group 2 | febuxostat 3 mg/kg/day | | | |
| Group 3 | enalapril 3 mg/kg/day | | | |
| Group 4 | febuxostat 3 mg/kg/day + enalapril 3 mg/kg/day | | | |
| | Group 1 | Group 2 | Group 3 | Group 4 |
| Before administration | 230 ± 2 | 230 ± 3 | 232 ± 5 | 231 ± 3 |
| 42nd day after administration | 226 ± 4 | 213 ± 5 | 220 ± 5 | 204 ± 5 |

TABLE 3

Effect of Febuxostat, Amlodipine and Combination Thereof on Blood Pressure

| Group | subject material and dose | | | |
|---|---|---|---|---|
| Group1 | tap water | | | |
| Group2 | febuxostat 3 mg/kg/day | | | |
| Group3 | amlodipine 3 mg/kg/day | | | |
| Group4 | febuxostat 3 mg/kg/day + amlodipine 3 mg/kg/day | | | |
| | Group 1 | Group 2 | Group 3 | Group 4 |
| Before administration | 227 ± 4 | 228 ± 4 | 228 ± 3 | 228 ± 3 |
| 14th day after administration | 229 ± 3 | 215 ± 4 | 219 ± 3 | 207 ± 5 |

TABLE 4

Effect of Febuxostat, Diltiazem and Combination Thereof on Blood Pressure

| Group | Test material and dose | | | |
|---|---|---|---|---|
| Group 1 | tap water | | | |
| Group 2 | febuxostat 3 mg/kg/day | | | |
| Group 3 | diltiazem 100 mg/kg/day | | | |
| Group 4 | febuxostat 3 mg/kg/day + diltiazem 100 mg/kg/day | | | |
| | Group 1 | Group 2 | Group 3 | Group 4 |
| Before administration | 231 ± 4 | 230 ± 5 | 229 ± 4 | 228 ± 5 |
| 42nd day after administration | 233 ± 3 | 227 ± 4 | 231 ± 4 | 224 ± 5 |

INDUSTRIAL APPLICABILITY

The present invention can be used to treat or prevent hypertension or high-normal blood pressure.

The invention claimed is:

1. A therapeutic method for hypertension or high-normal blood pressure comprising administering (a) and (b) in an amount which is more effective than an additive effect for the therapy of hypertension or high-normal blood pressure to a patient in need thereof:
   (a) 2-(3-cyano-4-isobutyloxyphenyl)-4-methyl-5-thiazole carboxylic acid or a pharmaceutically acceptable salt thereof,
   (b) losartan, candesartan, valsartan, telmisartan, olmesartan, irbesartan, pratosartan, eprosartan or a pharmaceutically acceptable salt thereof.

2. The therapeutic method for hypertension or high-normal blood pressure according to claim 1, wherein (b) is losartan or candesartan.

3. The therapeutic method for hypertension or high-normal blood pressure according to claim 1, wherein (a) and (b) are administered simultaneously.

4. The therapeutic method for hypertension or high-normal blood pressure according claim 1, wherein (a) and (b) are administered separately.

* * * * *